US011988608B2

(12) United States Patent
Maltas (10) Patent No.: US 11,988,608 B2
(45) Date of Patent: May 21, 2024

(54) METHOD FOR DETERMINING THE PRESENCE OF AN ACIDIC SULFIDE SPECIES IN A NON-AQUEOUS LIQUID USING A METAL COMPLEX DYE (71) Applicant: INNOSPEC LIMITED, Ellesmere Port (GB)

(72) Inventor: Philip Maltas, Ellesmere Port (GB)

(73) Assignee: INNOSPEC LIMITED, Ellesmere Port (GB)

( * ) Notice: Subject to any disclaimer, the term of this patent is extended or adjusted under 35 U.S.C. 154(b) by 131 days.

(21) Appl. No.: 16/633,349

(22) PCT Filed: Aug. 6, 2018

(86) PCT No.: PCT/GB2018/052245
§ 371 (c)(1),
(2) Date: Jan. 23, 2020

(87) PCT Pub. No.: WO2019/034844
PCT Pub. Date: Feb. 21, 2019

(65) Prior Publication Data
US 2021/0156806 A1 May 27, 2021

(30) Foreign Application Priority Data
Aug. 14, 2017 (GB) ..................... 1713017

(51) Int. Cl.
*G01N 21/78* (2006.01)
*G01N 21/27* (2006.01)
(Continued)

(52) U.S. Cl.
CPC .......... *G01N 21/78* (2013.01); *G01N 21/272* (2013.01); *G01N 21/293* (2013.01); *G01N 33/2823* (2013.01); *G01N 33/287* (2013.01)

(58) Field of Classification Search
CPC .. G01N 21/272; G01N 21/78; G01N 33/2823; G01N 33/287; G01N 21/293
(Continued)

(56) References Cited

U.S. PATENT DOCUMENTS 1,970,583 A * 8/1934 Stagner ................. C10G 19/00
208/205
2,722,500 A * 11/1955 Rippie ................ C07C 7/14875
208/236

(Continued)

FOREIGN PATENT DOCUMENTS

RU 2315297 C1 * 1/2008
WO 2016028768 A1 2/2016

OTHER PUBLICATIONS

Choi, M. G. et al., Chemical Communications 2009, 7390-7392.*
(Continued)

*Primary Examiner* — Arlen Soderquist
(74) *Attorney, Agent, or Firm* — Shumaker, Loop & Kendrick, LLP (57) ABSTRACT

A method for determining the presence of an acidic sulfide species in a liquid sample of an industrial or environmental material. The method includes the step of contacting the sample or an extract thereof with a composition including a metal complex dye compound in which the electromagnetic absorption spectrum of the metal complex dye compound changes upon reaction with an acidic sulfide species.

15 Claims, 5 Drawing Sheets (51) Int. Cl.
*G01N 21/29* (2006.01)
*G01N 33/28* (2006.01)

(58) Field of Classification Search
USPC .......................................... 436/120–121, 171
See application file for complete search history.

(56) References Cited

U.S. PATENT DOCUMENTS

| | | | | | |
|---|---|---|---|---|---|
| 3,199,946 | A * | 8/1965 | Fujita | .................. | C10K 1/20 |
| | | | | | 423/576.5 |
| 3,660,035 | A * | 5/1972 | Marsh | .................. | G01N 33/287 |
| | | | | | 204/405 |
| 4,174,202 | A * | 11/1979 | Simpson | .............. | G01N 31/02 |
| | | | | | 422/403 |
| 5,083,868 | A * | 1/1992 | Anderson | ............ | G01N 21/251 |
| | | | | | 356/402 |
| 5,397,708 | A * | 3/1995 | Lessard | ................ | G01N 33/287 |
| | | | | | 548/549 |
| 5,529,841 | A * | 6/1996 | Neihof | ................ | G01N 31/224 |
| | | | | | 95/8 |
| 6,969,613 | B1 * | 11/2005 | Ebinuma | ............... | C12Q 1/527 |
| | | | | | 435/130 |
| 8,271,234 | B1 * | 9/2012 | Cunningham | ............ | F41H 1/00 |
| | | | | | 702/188 |
| 2003/0166292 | A1 * | 9/2003 | Collins | .................. | G01N 31/22 |
| | | | | | 436/80 |
| 2005/0157304 | A1 * | 7/2005 | Xiao | ..................... | G01N 21/552 |
| | | | | | 356/446 |
| 2005/0165554 | A1 * | 7/2005 | Betancourt | ............. | E21B 49/08 |
| | | | | | 702/11 |
| 2005/0227369 | A1 * | 10/2005 | Richardson | ........ | G01N 33/2876 |
| | | | | | 422/400 |
| 2008/0165361 | A1 * | 7/2008 | Kauffman | .............. | G01N 31/22 |
| | | | | | 356/402 |
| 2008/0206874 | A1 * | 8/2008 | Manka | ............... | G01N 33/2888 |
| | | | | | 436/2 |
| 2009/0107667 | A1 * | 4/2009 | Mullins | .................. | G01N 21/77 |
| | | | | | 166/250.12 |
| 2009/0137054 | A1 * | 5/2009 | Hoagland | .............. | B82Y 30/00 |
| | | | | | 436/102 |
| 2010/0269579 | A1 * | 10/2010 | Lawrence | .......... | G01N 33/2823 |
| | | | | | 73/152.23 |
| 2011/0011799 | A1 * | 1/2011 | Rozendal | ............. | C02F 1/4693 |
| | | | | | 210/203 |
| 2011/0033943 | A1 * | 2/2011 | Dessort | .................. | C01G 11/00 |
| | | | | | 436/119 |
| 2011/0315921 | A1 * | 12/2011 | Ramachandran | ...... | B01D 53/52 |
| | | | | | 210/749 |
| 2013/0201244 | A1 * | 8/2013 | Benedicto | ............ | G01J 3/027 |
| | | | | | 347/19 |
| 2015/0021490 | A1 * | 1/2015 | Han | .................... | G01N 1/4055 |
| | | | | | 250/372 |
| 2015/0160183 | A1 * | 6/2015 | Lee | ......................... | C10L 1/232 |
| | | | | | 546/171 |
| 2015/0359458 | A1 * | 12/2015 | Erickson | ............ | A61B 5/14539 |
| | | | | | 382/133 |
| 2016/0025699 | A1 * | 1/2016 | Rodgers | .............. | G01N 33/287 |
| | | | | | 436/91 |
| 2017/0212272 | A1 | 7/2017 | Monteiro | | |
| 2017/0268997 | A1 * | 9/2017 | Barrios | .................. | G01N 21/64 |
| 2017/0298281 | A1 * | 10/2017 | Weers | ..................... | C10G 21/16 |
| 2018/0045705 | A1 * | 2/2018 | Ashtekar | ............... | E21B 49/082 |
| 2018/0369428 | A1 * | 12/2018 | Yoo | .................... | A61K 51/0482 |
| 2019/0322951 | A1 * | 10/2019 | Roe | .......................... | C02F 1/50 |

OTHER PUBLICATIONS

Feng, L. et al., Analytica Chimica Acta 2012, 743, 1-8.*
Tang, L. et al., Inorganic Chemistry Communications 2013, 36, 100-104.*
Tang, L. et al., Bulletin of the Korean Chemical Socciety 2013, 34, 2905-2908.*
Hai, Z. et al., Analytical Chemistry 2015, 87, 2678-2684.*
Li. X. et al., Biosensors and Bioelectronics 2015, 65, 302-306.*
Ariza-Avidad, M. et al., Analytica Chimica Acta 2015, 872, 55-62.*
Sun M. et al., Inorganic Chemistry 2015, 54, 3766-3772.*
Ren, K. et al., Polyhedron 2016, 104, 99-105.*
Choi, M. M. F. et al., Sensors and Actuators B 2003, 90, 211-215.*
Toda, K. et al., Analytica Chimica Acta 2004, 511, 3-10.*
Wallace, K. J. et al., Sensors and Actuators B 2007, 120, 362-367.*
Ninh, H. P. et al., Sensors and Actuators B 2007, 125, 138-143.*
Sasakura, K. et al., Journal of the American Chemical Society 2011, 133, 18003-18005 and 18 pages of supporting information.*
Andruch, V. et al., Microchemical Journal 2012, 102, 1-10.*
Pandey, S. K. et al., Trends in Analytical Chemistry 2012, 32, 87-99.*
Hou, F. et al., Inorganic Chemistry 2012, 51, 2454-2460 and 9 pages of supporting information.*
Hou, F. et al., Dalton Transactions 2012, 41, 5799-5804 and 13 pages of supporting information.*
Toda, K. et al., Analytica Chimica Acta 2012, 741, 38-46.*
Bae, J. et al., Tetrahedron Letters 2014, 55, 1171-1174 and 10 pages of supplementary data.*
Al-Zahrani, I. et al., Journal of Chromatography A 2014, 1330, 97-102.*
Zhang, Z. et al., ACS Applied Materials & Interfaces 2014, 6, 6300-6307 and 8 pages of supporting linformation.*
Bhopate, D. P. et al., New Journal of Chemistry 2015, 39, 7086--7096 and 5 pages of supporting information.*
Kaushik, R. et al., Journal of Luminescence 2016, 171, 112-117 and 26 pages of supporting information.*
Mironenko, A. Y. et al., Sensors and Actuators B 2016, 225, 348-355.*
Song, G. et al., Analytical Letters 2016, 49, 1480-1491.*
Pla-Tolos, J. et al., Talanta 2016, 156-157, 79-86.*
Carpenter, T. S. et al., Sensors and Actuators B 2017, 253, 846-851.*
Cresser, M. S. et al., in "Instrumental Analysis of Pollutants" Hewitt, C. N. (ed.), 1991, 99-145.*
Weil, R. R. et al., American Journal of Alternative Agriculture 2003, 18, 3-17.*
Petruci, J. F. S. et al., Microchemical Journal 2013, 106, 368-372.*
Field, E. et al., Industrial and Engineering Chemistry Aanlytical Edition 1946, 18, 665-667. (Year: 1946).*
Wolf, J. R. et al., SPE paper 7971 1971, 4 pages. (Year: 1971).*
International Search Report (ISR) fand Written Opinion for PCT/GB2018/052245 dated Nov. 19, 2018 (13 pages).
Dengqing Zhang et al., "Highly selective and sensitive colorimetric probe for hydrogen sulfide by a copper (II) complex of azo-dye based on chemosensing ensemble approach", Spectrochimica Acta. Part A: Molecular and Biomolecular Spectroscopy, vol. 90, p. 35-39, Jan. 8, 2012.
Domenico Paone et al., "Praktische Einfuhrung in die Chemie Integriertes Praktikum: Versuch 1-7 (KOG) Komplexgleichgewicht" May 16, 2012, XP055522263 (Cited in ISR for PCT/GB2018/052245 provided herein per MPEP 609.04(a)(III)).
Ying Hu et al., "A multi-responsive cyanine-based colorimetric chemosensor containing dipicolylamine moieties for the detection of Zn(II) and Cu(II) ions", Sensors and Actuators B: Chemical, vol. 230, p. 40-45 (2016).

* cited by examiner

METHOD FOR DETERMINING THE PRESENCE OF AN ACIDIC SULFIDE SPECIES IN A NON-AQUEOUS LIQUID USING A METAL COMPLEX DYE

TECHNICAL FIELD AND BACKGROUND

The present invention relates to a kit and method for measuring the concentration of hydrogen sulfide ($H_2S$) and other acidic sulfide species in a liquid sample of an industrial or environmental material.

Hydrogen sulfide and other acidic sulfide species are known to be formed within the oil reservoir and thus they are an issue throughout the petroleum industry. They are an issue during the exploration, drilling, fracking, completion, production, storage and transport of crude oil. For example, crude oil, produced water from within the well, used fracking fluids, used water-flooding fluids and used drilling muds all may contain hydrogen sulfide.

Hydrogen sulfide and other acidic sulfide species are also problematic during the processing of crude oil, where it is liberated by processes such as hydro-processing, cracking and coking. Furthermore, they are known to be present in the liquids, distillation residues such as asphalt or bitumen and solids, such as coke, that are present in petroleum refineries. The acidic sulfide species may be present in petroleum refinery liquids such as liquid products, by-products, intermediates and waste streams.

Hydrogen sulfide and other acidic sulfide species are not just problematic for the petroleum industry. These compounds are also known to be present in waste waters, sewage, the effluent from tanneries and paper mills, geothermal fluids and thus geothermal power plants.

Hydrogen sulfide is highly toxic. It is very corrosive and can quickly damage machinery, storage tanks and pipelines. It is also poisonous to many catalysts.

Other sulfide species for example $HS^-$, $S^{2-}$ and RSH are also commonly found in industrial and environmental materials. These too can cause corrosion and may release toxic hydrogen sulfide gas.

It is therefore essential to be able to detect the presence of hydrogen sulfide and other sulfide compounds and to quantify the levels present in an industrial or environmental material. Agents are available to treat hydrogen sulfide but the amount of sulfide present needs to be determined to ensure these agents are dosed correctly. In some instances the testing and dosing must be done in a remote location and therefore requires a portable testing method.

Thus acidic sulphide species may be an issue anywhere where the acidic sulphide species occur naturally, or through man made intervention.

A common method of determining the concentration of hydrogen sulfide present in the liquid is to measure the content of hydrogen sulfide in the gas phase above the liquid in the container (i.e. the concentration of hydrogen sulfide in the "headspace") for bulk storage liquids. It is assumed that an equilibrium is reached between the hydrogen sulfide present in the bulk liquid and that in the headspace above the liquid. In such a method, the concentration of hydrogen sulfide in the headspace is measured (typically using a Drager tube), a reagent to treat the hydrogen sulfide is added, the system is again allowed to reach equilibrium and then the concentration of hydrogen sulfide in the headspace gas is retested. The process is repeated as necessary in an iterative manner, until the desired hydrogen sulfide content is achieved.

However there are a number of issues with such methods. The Drager tubes can only detect $H_2S$ in the gaseous phase. Other sulfide species or mercaptans which may produce $H_2S$ are not detected. Furthermore, measurement of $H_2S$ present in the gaseous phase is difficult to calibrate with the concentration of $H_2S$ present in the liquid phase since this is dependent on several parameters such as the volume of the headspace, the temperature, the pressure and the nature of the liquid. It is therefore difficult to convert a headspace reading taken from a Drager tube to an appropriate treat rate for delivery to the $H_2S$ present in the bulk liquid. Thus the method is laborious and inaccurate.

Direct measurement of the concentration of hydrogen sulfide in a liquid phase can be carried out using liquid phase extraction according to a standard test method, for example IP570 or ASTM D7621.

However this method does not detect other sulfide or mercaptan species. Furthermore the equipment is typically slow to use, requiring at least 45 minutes for set-up and calibration and a subsequent 30-45 minutes per test. Yet another challenge is that the equipment requires external power, weighs in excess of 15 kg and requires several accessories (including a weighing device) which make it difficult to transport and use in the field. In addition such liquid $H_2S$ detectors are typically expensive to buy and run.

Thus the current standard test methods are unsuitable for quickly and accurately testing for hydrogen sulfide in remote locations where there is no laboratory testing available, for example in a cargo hold. The lack of a suitably quick and accurate test causes undesirable delay in treatment of the material to mitigate the hydrogen sulphide.

Having a portable test method that allows testing for hydrogen sulfide in remote locations would significantly reduce the health and safety risk associated with working in these areas.

SUMMARY

There is thus a need for an improved means by which the concentration of hydrogen sulfide in a material can be determined quickly and accurately. It is also desirable to detect other acidic sulfide species.

DETAILED DESCRIPTION

According to a first aspect of the present invention there is provided a method for determining the presence of an acidic sulfide species in a liquid sample of an industrial or environmental material, the method comprising the steps of:
(a) contacting the sample or an extract thereof with a composition comprising a metal complex dye compound;

wherein the electromagnetic absorption spectrum of the metal complex dye compound changes upon reaction with an acidic sulfide species.

The present invention relates to a method for determining the presence of an acidic sulfide species. It will be appreciated by the skilled person that if the presence of an acidic sulfide species is not determined an absence thereof can be inferred.

By acidic sulfide species we mean to refer to any compound including a sulfur atom having a −2 oxidation state bound to an acidic hydrogen atom or the conjugate base thereof. The conjugate base refers to the anion formed on removal of the acidic hydrogen atom.

Suitable acidic sulfide species include $H_2S$; compounds containing the ions $HS^-$ or $S^{2-}$; and any compound or ion containing the functional groups —SH, —S$^-$, —S—SH, —S—S$^-$, —S$_n$H, —S$_{(n-1)}$S$^-$.

Suitable acidic sulfide species include hydrogen sulfide ($H_2S$) or its anion ($HS^-$), sulfide anion ($S^{2-}$); thiols (RSH) and their conjugate base (RS$^-$); hydrodisulfides (R—S—S—H) and their conjugate base (R—S—S$^-$); or hydropolysulfides (RS$_n$H) and their conjugate base (RS$_{n-1}$S$^-$). R may be, for example, an optionally substituted alkyl, alkenyl, aryl, aralkyl, alkaryl or heterocyclic group. However it will be appreciated that the specific nature of the R group is unimportant since it is the sulphur containing functional group that is detected.

Preferably the acidic sulfide species is selected from hydrogen sulfide ($H_2S$), sulfide anion ($S^2$); hydrosulfide ion ($HS^-$); compounds including a thiol group (—SH) and their conjugate base (—S$^-$).

Preferably the present invention provides a method of determining the presence of hydrogen sulfide or a source thereof in a sample. By hydrogen sulfide or a source thereof we mean to refer to hydrogen sulfide or a compound which readily generates hydrogen sulfide. Compounds which generate hydrogen sulfide include the thiol, disulfide and polysulfide species mentioned above.

Suitably the present invention provides a method of determining the presence of hydrogen sulfide.

The present invention relates to a method of determining the presence of an acidic sulfide species in a liquid sample of an industrial or environmental material. The method may also be used to measure the amount of acidic sulfide species present in the liquid sample.

The method may be used to detect acidic sulfide species in a liquid sample obtained from any type of industrial or environmental material.

The invention is carried out on a sample that is in liquid form. However the material from which the sample is obtained may be in a liquid, solid or gaseous form.

The industrial or environmental materials may include solids, liquids or gasses that are obtained from any industries or environments where an acidic sulfide species may be present.

The industrial material may be a product, by-product, intermediate or waste stream obtained from an industry and may be solid or a fluid, such as liquid or a gas. For example, the sample of industrial material may be sourced from an oil well, a petroleum refinery, the cargo hold of a vehicle transporting crude oil or petroleum products, an oil pipeline, a farm slurry pit, sewage works, paper mill or tannery. Thus, industrial materials may include crude oil, produced water, petroleum refinery liquids, coke, asphalt or bitumen, used fracking fluids, used water-flooding fluids, a geothermal fluid or sour gas etc.

The sample of environmental material may be taken from a non-industrial location where it is desirable to determine the amount of acidic sulfide species present. For example, the source of the environmental material may be a petroleum reservoir, geothermal reservoir, rainwater reservoir or lake or river. The environmental material may be solid or a fluid such as a liquid or a gas.

The examples of industrial and environmental materials listed above are suitable for use in the test method as described herein, however they are not intended to be limiting.

The industrial or environmental material can be a solid, a liquid or a gas. As the skilled person would appreciate when the industrial or environmental material is a solid, a gas or highly viscous liquid, a pre-treatment step is needed to provide a liquid sample. This pre-treatment step should be selected to ensure that any acidic hydrogen species present in the material are collected in the liquid sample to be tested. Such a pretreatment step may also be useful in the case of coloured liquids or liquids not miscible with water.

The selection of an appropriate pre-treatment step will be within the competence of the person skilled in the handling of solids, viscous liquids or gasses. The skilled person would thus be able to obtain a liquid sample for use in the method from any environmental or industrial material. For viscous liquids, pre-treatment methods may include, for example, addition of another liquid component to lower the viscosity or using an extraction technique to remove the acidic sulfide species. For solid or gaseous materials, a pre-treatment technique may involve contacting the solid or gas with a liquid into which the acidic sulfide species dissolve. Such techniques for removing acidic sulfide species are known in the art and may further include changing the temperature, pressure or pH to facilitate the transition of the acidic sulfide species into the liquid. Such a pretreatment step may also be useful in the case of coloured liquids or liquids not miscible with water.

Gaseous industrial or environmental materials that may be subjected to a pre-treatment step to provide the liquid sample include sour gas, gasses formed in the refining of crude oil, and gasses liberated in the transport of crude oil or petroleum liquids, especially those found in the headspace of a storage tank or cargo storage or in pipelines.

Solid environmental or industrial materials that may be pre-treated include hydrocarbonaceous materials for example: paraffin waxes, distillation residues, asphalt, bitumen or coke. The resulting liquid sample comprising the acidic sulfide species may require additional purification, for example filtration to remove solid particles, before it can be used in the method of the first aspect. Such methods are known to those skilled in the art.

In some embodiments the present invention may provide a method for determining the presence of an acidic sulfide species in an industrial or environmental material, the method comprising the steps of:

(x) preparing a liquid sample of the industrial or environmental material, and
  (a) contacting the sample or an extract thereof with a composition comprising a metal complex dye compound;
wherein the electromagnetic absorption spectrum of the metal complex dye compound changes upon reaction with an acidic sulfide species.

Suitably the liquid sample is prepared in step (x) in a manner to ensure that any acidic sulfide species present in the material are provided in the liquid sample. In some embodiments in which the industrial or environmental material is a solid or a gas, step (x) may suitably involve contacting the solid or gaseous material with a liquid in which acidic sulfide species are soluble or readily dispersed.

Preferably, the industrial or environmental material is a liquid.

More preferably the industrial or environmental material is directly used as the liquid sample.

In such embodiments step (x) simply involves collecting a portion of the industrial or environmental material.

In one embodiment the industrial or environmental material may be located in an area where laboratory testing is suitable for determining the content of acidic sulfide species, for example a petroleum refinery, sewage works, paper mill, tannery.

In another embodiment the industrial or environmental material may be located in a remote location where laboratory testing is not suitable for determining the content of acidic sulfide species. For example a remote location may be: an oil well—especially those in sour gas containing oil fields, an oil rig, the cargo hold of a transport vehicle e.g. a ship or railcar, a geothermal well, a storage tank, a point on an oil pipeline, a farm slurry pit or a rainwater storage unit that is susceptible to bacterial contamination.

The industrial or environmental material may be selected from fluids in or extracted from an oil well; products, by-products, intermediates and waste streams from refineries and other industries; water; sewage; and geothermal fluids.

Fluids in or extracted from an oil well may be selected from: crude oil; gas condensate; gas; sour gas; produced water; drilling fluids; fracturing fluids; water flooding fluids.

The drilling fluids and fracturing fluids may preferably be selected from drilling fluids in use, used drilling fluids, fracturing fluids in use and used fracturing fluids.

Products, by-products, intermediates and waste streams from refineries and other industries include solids and fluids such as liquids or gases.

Other industries may be selected from biofuel production, farming, tanneries, paper mills and power.

In a preferred embodiment, the industrial or environmental material may be selected from: crude oil; gas condensate; gas; sour gas; produced water; drilling fluids in use; used drilling fluids; fracturing fluids in use; used fracturing fluids; water flooding fluids; solid products, by-products, intermediates and waste streams from refineries; fluid products, by-products, intermediates and waste streams from refineries; and solid and liquid products, by-products, intermediates and waste streams from other industries such as biofuel production, farming, tanneries, paper mills and power.

The present invention is especially useful for determining the presence of acidic sulfide species in a crude oil sample or a petroleum refinery liquid.

In some embodiments the present invention is used for determining the presence of acidic sulfide species in a crude oil sample.

In some embodiments the present invention is used for determining the presence of acidic sulfide species in a petroleum refinery liquid.

The liquid sample may be an aqueous liquid, a non-aqueous liquid or a mixture thereof.

Step (a) involves contacting the liquid sample or an extract thereof with a composition comprising a metal complex dye compound. This may be referred to herein as simply "the composition comprising a dye compound" and the metal complex dye compound may be referred to as "the dye compound".

In some embodiments the composition comprising the dye compound is directly contacted with the liquid sample.

In some embodiments the composition comprising the dye compound is contacted with an extract of the liquid sample, as is later described herein.

In other embodiments the composition comprising the dye compound may be impregnated on a solid substrate which is contacted with the liquid sample or an extract thereof, as is later described herein.

In all embodiments the invention involves contacting the liquid sample or an extract of the liquid sample with a composition comprising a metal complex dye compound wherein the electromagnetic absorption spectrum of the metal complex dye compound changes upon reaction with an acidic sulfide species.

When an acidic sulfide species is present in the liquid sample or an extract thereof this reacts with the metal complex dye compound. The resulting product has a different electromagnetic absorption spectrum to that of the initial dye compound. For the avoidance of doubt by stating that the electromagnetic absorption spectrum of the dye compound changes upon reaction with an acidic sulfide species, it is meant that the electromagnetic absorption spectrum of the dye compound-sulfide product is different to the initial electromagnetic absorption spectrum of the dye compound prior to reaction with the acidic sulfide species.

The metal complex dye compound includes a chromophore. This is the light absorbing portion of the molecule. The chromophore of the dye compound used in the present invention may absorb light in any region of the electromagnetic spectrum. Preferably the chromophore absorbs light in the ultraviolet (UV), visible or infrared (IR) region of the electromagnetic spectrum.

Thus the change in the electromagnetic absorption spectrum of the dye compound may occur in the UV, visible or IR region of the electromagnetic spectrum.

The change in the electromagnetic absorption spectrum may be a change in the intensity of absorption at a single wavelength or a change in the wavelength of an absorption maximum.

Preferably the change in the electromagnetic absorption spectrum of the dye compound occurs in the visible region. Suitably the dye compound undergoes a visible colour change upon reaction with an acidic sulfide species.

In one embodiment the dye compound may change between colourless and coloured (either starting coloured or starting colourless). In another embodiment the dye compound is a first colour prior to contact with an acidic sulfide species and a second colour after contact with an acidic sulfide species wherein the first colour and the second colour are different. In some embodiments the first colour and second colour are sufficiently different as to be readily distinguishable by the naked eye.

Any metal complex dye compound whose electromagnetic absorption spectrum changes upon reaction with an acidic sulfide species may be used. Preferably a metal complex dye compound which undergoes a visible colour change is used.

Preferred are metal complex dye compounds that readily react with acidic sulfide species.

After it has been reacted with an acidic sulfide species, the dye compound suitably absorbs light at least one wavelength in the region 300-700 nm, preferably at least one wavelength in the range 400 to 600 nm.

Suitable metal complex dye compounds for use herein include fluorescein derivatives such as compounds 1, 2 and 3 below, dipyridine metal complexes, phthalocyanines, porphyrins, and ferrocenes.

Preferred dye compounds are metal complexes of azo dyes.

Preferred dye compounds include copper (II) complexes of azo dyes.

One especially preferred dye compound is the copper (II) chloride complex of 1-(2-pyridylazo)-2-naphthol.

The composition comprising the dye compound may consist essentially of the metal complex dye compound or it may further comprise a diluent or carrier and/or one or more further components.

In some embodiments the composition comprising the metal complex dye compound is carried on a solid substrate. In some embodiments the solid substrate is paper.

In preferred embodiments the composition comprising the dye compound is a liquid composition. Preferably the composition comprises the metal complex dye compound and one or more solvents.

Preferably the composition comprising the dye compound is at least partially miscible with a non-aqueous composition.

Preferably the composition comprising the dye compound is at least partially miscible with an aqueous composition.

Preferably the composition comprising the dye compound is at least partially miscible with aqueous compositions and non-aqueous compositions.

Preferably the composition comprising the dye compound comprises a water miscible solvent selected from alcohols, esters, nitriles, amides, ethers, aromatics, ketones, aldehydes, chlorinated alkyls and water.

Preferably the composition comprising the dye compound comprises an alcohol. Preferred alcohols are water miscible alcohols. Suitable alcohols include monohydric alcohols and polyhydric alcohols. Monohydric alcohols are preferred. Preferably the composition comprising the dye compound comprises methanol, ethanol or isopropanol. Most preferably the composition comprising the dye compound comprises ethanol.

Preferably the composition comprising the dye compound comprises at least 10 wt % ethanol, preferably at least 40 wt %, more preferably at least 60 wt %, for example at least 80 wt %.

In some preferred embodiments the composition comprising the dye compound comprises, as solvents, a mixture of ethanol and water. The ratio of water to ethanol may be from 99:1 to 1:99. Suitably the composition comprises from 50 to 99 wt % ethanol and from 1 to 50 wt % water, for example from 85 to 95 wt % ethanol and from 5 to 15 wt % water.

The dye compound is suitably present in the composition contacted with the liquid sample or an extract thereof in an amount of at least 0.00001 wt %, suitably at least 0.00005 wt %, preferably at least 0.0001 wt %, suitably at least 0.0005 wt %, for example at least 0.001 wt %.

The dye compound is suitably present in the composition contacted with the liquid sample or an extract thereof in an amount of up to 5 wt %, suitably up to 1 wt %, preferably at least up to 0.1 wt %, suitably up to 0.05 wt %, for example up to 0.01 wt % or up to 0.005 wt %.

Preferably the composition comprising the dye compound has a pH of from 4 to 10.

In some preferred embodiments the composition comprising the dye compound has a pH of between 7 and 8.

The composition comprising the dye compound may further comprise a buffer. Suitable buffers will be known to the person skilled in the art and include buffer solutions comprising citric acids, phosphates, acetic acid, imidazoles, carbonate, Tris(hydroxymethyl)aminomethane, borate, phthalate, or salts and combinations thereof; for example TRIS-HCl (Trizma), citric acid-sodium citrate, citric acid-disodium phosphate ($Na_2HPO_4$), acetic acid-Sodium acetate, imidazole-HCl buffer, sodium carbonate-sodium bicarbonate, tris(hydroxymethyl) aminomethane, borate and phthalates buffers.

One especially preferred buffer for use herein is tris (hydroxymethyl)aminomethane and salts thereof, for example the hydrochloride salt.

In some preferred embodiments the composition contacted with a liquid sample or an extract thereof in step (a) comprises a metal complex dye compound, ethanol and a buffer solution. The ratio of buffer solution to ethanol is suitably from 100:1 to 1:100, preferably from 20:1 to 1:20. In a preferred embodiment the ratio of buffer solution to ethanol is suitably from 1:1 to 1:20, preferably from 1:5 to 1:15.

In some embodiments the composition comprising the dye compound is directly contacted with a liquid sample of the industrial or environmental material. Such a method in which an extract of the sample is not taken is suitable when the liquid sample does not interfere with the electromagnetic absorption spectrum of the dye compound and/or any background interference can be mitigated.

In some embodiments in step (a) involves the steps of:
(a1) contacting the liquid sample with an extraction composition to provide an aqueous extract; and
(a2) contacting the aqueous extract with a composition comprising a metal complex dye compound;
wherein the electromagnetic absorption spectrum of the metal complex dye compound changes upon reaction with an acidic sulfide species.

A method in which step (a) involves step (a1) and step (a2) may suitably be used in embodiments in which the liquid sample is coloured or opaque and/or when the dye compound is soluble in the coloured or opaque phase. Such a method may also be used when the liquid sample is non-aqueous and poorly miscible with water.

When the liquid sample comprises crude oil and/or a petroleum refinery product, for example, the present invention preferably involves step (a1) and step (a2).

Step (a1) involves contacting the liquid sample with an extraction composition. The extraction composition preferably comprises an aqueous component. The extraction composition preferably includes an aqueous component and a non-aqueous component.

The ratio of the aqueous component to the non-aqueous component may vary depending on the sample being tested. For example, the ratio may be from 100:1 to 1:100, from 10:1 to 1:10 or from 2:1 to 1:2.

The aqueous component is preferably a basic aqueous composition having a pH of more than 7.

Suitably the basic aqueous composition comprises water and a water soluble base. The water soluble base may be an organic base, an inorganic base or a mixture thereof. Suitable organic bases are water soluble alkoxides and basic amines. Preferred water soluble organic bases are sodium methoxide and triethylamine.

Preferably the basic aqueous composition comprises a basic ionic compound dissolved in water. Suitably the basic aqueous composition is a solution of a carbonate, hydroxide or hydrogen carbonate. Preferably the basic aqueous composition is a solution of an alkali metal hydroxide, preferably a solution of sodium hydroxide.

In a preferred embodiment the water soluble base is selected from sodium methoxide, triethylamine, an alkali metal hydroxide or combinations thereof.

Suitably the basic aqueous composition has a pH of at least 7, preferably at least 8, more preferably at least 9, suitably at least 10, for example 11 or 12.

In one embodiment the non-aqueous component of the extraction composition may comprise a base. Any base is suitable as long as the resulting sulfide salt can partition into an aqueous composition.

The non-aqueous component of the extraction composition preferably comprises an organic solvent. Any organic solvent may be used including aromatic and aliphatic solvents and mixtures of solvents. Suitably the organic solvent is not miscible with the composition comprising the metal complex dye compound.

Suitably the aqueous component and the non-aqueous component are immiscible.

Suitably in step (a1) the extraction composition is mixed with the liquid sample and the resultant mixture is agitated then allowed to settle. On settling the aqueous and non-aqueous phases will separate and the aqueous phase or a portion thereof can be collected. This aqueous extract is then contacted with the composition comprising a metal complex dye compound wherein the electromagnetic absorption spectrum of the metal complex dye compound changes upon reaction with an acidic sulfide species in step (a2).

Thus in the method of the present invention the liquid sample (step (a)) or an extract of the sample (step (a2)) is contacted with a composition comprising a metal complex dye compound wherein the electromagnetic absorption spectrum of the metal complex dye compound changes upon reaction with an acidic sulfide species.

After contacting the liquid sample or extract thereof with the composition comprising the dye compound the resultant mixture may be agitated.

In preferred embodiments the method of the present invention suitably involves a step (b) of examining the electromagnetic spectrum of the composition obtained in step (a).

Suitably step (b) involves examining the changed region of the electromagnetic absorption spectrum of the composition obtained in step (a).

In some embodiments the present invention provides a method for determining the presence of an acidic sulfide species in a liquid sample of an industrial or environmental material, the method comprising the steps of:
(a) contacting the liquid sample or an extract thereof with a composition comprising a metal complex dye compound wherein the electromagnetic absorption spectrum of the metal complex dye compound changes upon reaction with an acidic sulfide species; and
(b) examining the changed region of the electromagnetic absorption spectrum of the composition obtained in step (a).

In some embodiments the present invention provides a method for determining the presence of an acidic sulfide species in a liquid sample of an industrial or environmental material, the method comprising the steps of:
(a1) contacting the liquid sample of the industrial or environmental material with an extraction composition to provide an aqueous extract;
(a2) contacting the aqueous extract with a composition comprising a metal complex dye compound wherein the electromagnetic absorption spectrum of the metal complex dye compound changes upon contact with an acidic sulfide species; and
(b) examining the changed region of the electromagnetic absorption spectrum of the composition obtained in step (a2).

Preferably step (b) involves examining the electromagnetic absorption spectrum of the composition obtained in step (a). Examining the electromagnetic absorption spectrum may involve measuring or recording the electromagnetic absorption spectrum or it may simply involve observing the electromagnetic absorption spectrum.

Preferably step (b) involves examining the changed region of the electromagnetic absorption spectrum. Preferably the changed region is the UV, visible or IR region of the electromagnetic absorption spectrum. Preferably it is the visible region.

The electromagnetic absorption spectrum of the dye compound changes upon reaction with an acidic sulfide species. This change occurs due to a reaction between the acidic sulfide species and the dye compound. The reaction suitably affects in some way the chromaphore moiety of the dye compound.

Preferably the sulfide reacts quickly with the dye compound. Preferably the reaction occurs at ambient temperature (typically 20-25° C.). Preferably the reaction is complete within 30 minutes, preferably within 10 minutes, suitably within 5 minutes, for example within 1 minute.

In some embodiments step (b) involves observing the colour of the resultant composition. For the avoidance of doubt this is the colour of the composition obtained when the composition comprising the dye compound is contacted with the liquid sample or the aqueous extract of the sample.

In some embodiments the present invention provides a method for determining the presence of an acidic sulfide species in a liquid sample of an industrial or environmental material, the method comprising the steps of:
 (a) contacting the liquid sample or an extract thereof with a composition comprising a metal complex dye compound which undergoes a colour change upon contact with an acidic sulfide species; and
 (b) observing the colour of the resultant composition.

In some embodiments the present invention provides a method for determining the presence of an acidic sulfide species in a liquid sample of an industrial or environmental material, the method comprising the steps of:
 (a1) contacting the liquid sample of the industrial or environmental material with an extraction composition to provide an aqueous extract;
 (a2) contacting the aqueous extract with a composition comprising a metal complex dye compound which undergoes a colour change upon contact with an acidic sulfide species; and
 (b) observing the colour of the resultant composition.

In some embodiments the dye is a metal ligand complex dye. In such embodiments the acidic sulfide species may react with the metal and displace the dye as a ligand. In such embodiments the ligand portion of the dye molecule (L) has a different electromagnetic absorption spectrum, preferably a different colour, when it is coordinated to the metal (M) compared with when it is not coordinated. Such a reaction scheme may be illustrated as follows:

or

In one preferred embodiment, the dye selectively reacts with the acidic sulfide species over other common anions. Preferably the dye selectively reacts with the acidic sulfide species in the presence of: $F^-$ or $Cl^-$ or $Br^-$ or $I^-$ or $CO_3^{2-}$ or $HCO_3^-$ or $NO_2^-$ or $SO_4^{2-}$ or $H_2PO_4^{2-}$ or $NO_3^-$ or $CN^-$ or $CH_3CO_2^-$ or combinations thereof.

Some preferred dye compounds are metal-azo dye complexes, for example copper-azo dye compounds.

One example of a suitable dye compound is the copper (II) chloride complex of 1-(2-pyridylazo)-2-naphthol, which react with acidic sulfide species as follows:

In some embodiments the method of the present invention may provide a qualitative assessment of whether or not there are any acidic sulfide species present in the liquid sample. In such embodiments the user will be aware that the liquid sample will absorb light at a particular wavelength, if sulfide is present and at a different wavelength if no sulfide is present.

Suitably the dye compound absorbs light at an initial wavelength before it is reacted with an acidic sulfide compound and at a final wavelength after reaction with the acidic sulfide compound.

Preferably the light absorbed is in the visible region of the electromagnetic spectrum and the dye compound may be regarded as having an initial colour and a final colour. The final colour will appear if an acidic sulfide species is present. In such embodiments step (b) may simply involve observing the colour of the resultant composition and noting the presence of the final colour.

In some embodiments the method of the present invention may be used to provide a quantitative assessment of the concentration of acidic sulfide species present in the liquid sample. In such embodiments step (b) will involve measuring the intensity of light absorbed at a particular wavelength or wavelengths in the resultant composition, for example measuring the absorption of one or more wavelengths of visible light.

In embodiments in which a quantitative assessment of sulfide concentration is carried out, the volume/mass of the liquid sample, the volume/mass of the extraction composition when used and the volume/mass of the composition comprising the dye compound should be known.

The concentration of the dye compound in the composition in which it is present can be known. When this is directly mixed with the liquid sample, the acidic sulfide species present in the sample will react with the dye compound. The higher the concentration of sulfide present in the sample, the greater number of dye molecules will react and change absorption spectrum, leading to a greater number of dye molecules that absorb light at the final wavelength and a lower concentration that absorb light at the initial wavelength. Thus measuring the intensity of the absorption at a particular wavelength or wavelengths when the sample is mixed with the composition comprising the dye compound can give an indication of the concentration of acidic sulfide species present in the sample.

In the present invention a dye compound is suitably selected for which absorption at the final wavelength increases in intensity as the reaction with an acidic sulfide species progresses.

Suitably the intensity of absorption at the final wavelength is proportional to the concentration of acidic sulfide species present in the composition.

In the present invention a dye compound is suitably selected for which the absorption at the initial wavelength decreases in intensity as the reaction with an acidic sulfide species progresses. Suitably the intensity of absorption at the initial wavelength is inversely proportional to the concentration of acidic sulfide species present in the composition.

When the liquid sample is opaque, coloured or highly oleophilic it may be first contacted with an extraction composition to obtain an aqueous extract which aqueous extract is then contacted with the composition comprising the dye compound. For a quantitative assessment a known volume of the sample is mixed with a known volume of extraction composition. The mixture is suitably agitated and because the aqueous layer is basic any acidic sulfide species present in the sample are suitably taken up into the aqueous layer. A known concentration of the aqueous layer may then be contacted with a known volume of the composition comprising the dye compound. Again the extent of the change in absorption spectrum, for example the colour change is proportional to the concentration of sulfide present in the extract and hence originally present in the sample.

Suitably the concentration of dye compound present in the composition contacted with the liquid sample or extract thereof is selected to ensure that there is an excess of dye compound compared with the expected concentration of acidic sulfide species so that the concentration of sulfide can be accurately measured.

In some preferred embodiments step (b) involves making a quantitative evaluation of the colour of the resultant composition.

The quantitative assessment of the colour of the liquid sample may suitably be made by comparing the colour of the resultant composition with that obtained using a reference material.

For some dye compounds the colour intensity of the resultant composition may be directly proportional to the concentration of the acidic sulfide species. Thus a calibration line may be established and used to quantify the concentration of acidic sulfide species.

For some dye compounds a direct linear relationship may not exist but by testing known concentration of acidic sulfide species a calibration curve can be established.

In some embodiments step (b) may involve a user visually comparing the colour of the resultant composition with a reference chart of results obtained using standard compositions.

In some embodiments in step (b) the absorption of light at one or more wavelengths is measured by spectroscopic means. The one or more wavelengths may be in the UV, visible or IR region of the electromagnetic spectrum.

Alternatively, a change in absorption spectra could be measured by comparing curve shape, e.g. using curve fitting algorithms, or by calculating the area under the curve for a given range of wavelengths. Another option for monitoring the spectroscopic change would be to track the change in absorbance wavelength ($\lambda$) for a specific intensity of signal (e.g. $\lambda_{max}$).

In some preferred embodiments in step (b) the colour of the resultant composition is measured using a spectrophotometer.

Suitably the spectrophotometer is used to measure the absorbance at least one wavelength in the region 300 to 700 nm, preferably at least one wavelength in the range 400 to 600 nm. Suitably the spectrophotometer is used to measure light at 420 to 490 nm or 520 to 590 nm or within both ranges.

In some embodiments the method may include measuring the absorbance of the composition comprising the dye compound at a particular wavelength before it is mixed with the liquid sample or extract thereof and then remeasuring the absorbance at the same wavelength after the composition is mixed with the sample or extract thereof. The difference between the readings can be used to calculate the amount of acidic sulfide species that must have been present in the sample.

The spectrophotometer could be used to measure the absorbance at two different wavelengths, for example at one wavelength that is absorbed by the dye when it has its initial colour and at one wavelength that is absorbed by the dye when it has its final colour. Measuring at two different wavelengths may help improve the accuracy of the results.

The reading from the spectrophotometer can be used to calculate the concentration of sulfide present in the resultant composition and hence the concentration that must have been present in the original liquid sample.

In some embodiments the user may carry out the necessary calculation. In other embodiments a table or chart may be provided where users can look up a concentration that corresponds to their reading from the spectrophotometer.

In some preferred embodiments the user may enter the reading from the spectrophotometer into a device which is programmed to calculate the sulfide concentration and display the result. The device may be programmed to convert the concentration of acidic sulfide species present into dosage rate for treating said sulfide species with a particular reagent.

The device may be a computer, tablet or mobile device. In some preferred embodiments the device is a smart phone.

According to a second aspect of the invention there is provided a kit for determining the presence or absence of an acidic sulfide species in a liquid sample of an industrial or environmental material, the kit comprising a composition comprising a dye compound which undergoes a colour change upon contact with an acidic sulfide species.

Preferred features of the second aspect are as defined in relation to the first aspect. Further features of the first and second aspects will now be described.

In a preferred embodiment the kit is portable.

In some preferred embodiments the composition comprising the dye compound is a solution of the dye compound in a suitable solvent, as defined in relation to the first aspect. The composition is provided in a suitable container. Preferably a known volume of the composition at a known concentration is provided.

In some embodiments the composition comprising the dye compound is provided in a unit dose form, i.e. a container provides an amount sufficient to determine the acidic sulfide species concentration in a single sample.

In other embodiments a bulk quantity of the composition comprising the dye may be provided along with means for collecting a known amount thereof, for example a syringe, pipette or balance.

In some embodiments the composition is carried on a solid substrate. In such embodiments the kit may comprise a plurality of substrates. In such embodiments the composition may be impregnated onto strips of a material such as paper. These strips can be dipped into the liquid sample or an extract thereof, for example in a similar manner to indicator papers.

In some preferred embodiments the kit further comprises means for collecting and/or storing the liquid sample. The kit may comprise a vessel for admixing the sample or an extract thereof with the composition comprising the dye compound. In some preferred embodiments the container comprising the composition comprising the dye compound is selected to provide space for the sample or an extract thereof to be added into the container. Suitably the composition comprising the dye compound is provided in an initially sealed container that can be opened and resealed and which has sufficient space to accommodate the sample or extract thereof and enable easy agitation and admixture of the resultant composition.

In some embodiments the kit further comprises an extraction composition. This is provided in a suitable container. Preferably it is provided in a container that can be opened and resealed and which has sufficient space to accommodate the sample and enable easy agitation and admixture of the sample and the extraction composition.

Further preferred features of the extraction composition are as defined in relation to the first aspect.

Preferably the kit further comprises means for accurately collecting a known amount of the sample, for example a known mass or volume. This may be a graduated pipette, a balance, a dispenser or a syringe and is suitably adapted to facilitate dosing the accurate amount fully into the extraction composition or the composition comprising the dye compound.

In some embodiments in which the kit includes an extraction composition it may further comprise means for collecting a known amount of the aqueous extract, for example a known mass or volume. This may be a graduated pipette, a balance, a dispenser or a syringe and is suitably adapted to facilitate dosing the accurate amount fully into the composition comprising the dye compound.

Optionally the kit comprises a set of instructions for use thereof.

Preferably the kit further comprises means for determining the concentration of sulfide present in the liquid sample. In some embodiments this may comprise a colour chart so that the colour of the sample can be matched with the chart.

In embodiments in which the composition comprising the dye compound is provided on a solid substrate the substrate can then be placed next to a colour chart and a corresponding value of sulfide concentration read by comparison.

In some preferred embodiments the kit further comprises means for measuring the absorbance of light at a particular wavelength. Preferably said means is a spectrometer, preferably a spectrophotometer.

In some embodiments the kit may further comprise a device for calculating the concentration of sulfide present in the sample from a spectrometer reading. Preferably the device is a portable device, for example, a mobile phone, tablet, laptop or calculator.

In some embodiments the kit may further include a balance. This may be used to weigh the sample. In some embodiments a container comprising either the extraction composition and/or the composition comprising the dye compound may be weighed before and after the addition of the sample or an extract thereof and the weight of the sample calculated by determining the difference.

In preferred embodiments the kit of the second aspect comprises:
a container comprising a composition comprising a dye compound which undergoes a colour change upon contact with an acidic sulfide species;
a container comprising an extraction solution;
means for collecting a known amount of a liquid;
instructions for use; and
a photospectrometer; and
a device, preferably a portable device, programmed to calculate the concentration of acidic sulfide species present in the sample from a spectrophotometer reading.

Because the kit of the present invention is portable, it can be used to test an industrial or environmental material sourced from a remote location. The remote location may be an oil well (especially those in sour gas containing oil fields), a geothermal well, an oil rig, the cargo hold of a transport vehicle (e.g. a ship or railcar), a storage tank, a point on a pipeline, a farm slurry pit, or rainwater storage that is susceptible to bacterial contamination.

Preferably, the remote location is selected from an oil well, a geothermal well, the cargo hold of a transport vehicle e.g. a ship or railcar, a storage tank or a point on a pipeline.

In an embodiment, the remote location is the cargo hold of a transport vehicle, e.g. a ship or railcar.

The kit and method enable a user to determine the amount of acidic sulfide species present in an industrial or environmental material. This allows the user to treat the material with an appropriate amount of a reagent to mitigate the presence of the acidic sulfide species.

The present invention enables the user to test and treat an industrial or environmental material rapidly. This "Quick to Treat" aspect is a significant advantage of the present invention.

According to a third aspect of the present invention there is provided a method of treating an industrial or environmental material to combat the presence of acidic sulfide species, the method comprising:
(x) preparing a liquid sample of the industrial or environmental material;
(a) contacting the liquid sample or an extract thereof with a composition comprising a metal complex dye compound wherein the electromagnetic absorption spectrum of the metal complex dye compound changes upon reaction with an acidic sulfide species; and
(b) examining the changed region of the electromagnetic absorption spectrum of the composition obtained in step (a);
(c) using the electromagnetic absorption spectrum examined in step (b) to calculate the amount of acidic sulfide species present in the liquid sample and hence in the industrial or environmental material; and
(d) treating the industrial or environmental material with an agent that mitigates the presence of the acidic sulfide species.

Steps (a) and (b) of the method of the third aspect are preferably as described in relation to the first aspect.

In preferred embodiments in which the industrial or environmental material is a liquid, step (x) may involve simply collecting a sample of this liquid.

In embodiments in which the industrial or environmental material is a solid or a gas, step (x) may involve contacting the solid or gaseous material with a liquid into which any acidic sulfide species present in the material are soluble or readily dispersed.

Step (c) involves using the electromagnetic absorption spectrum to calculate the amount of acidic sulfide species present in the liquid sample and hence in the industrial or environmental material. In some embodiments this calculation may be carried out by the user. In other embodiments values of absorption may be input into a device, wherein the device is programmed to perform the calculation.

Step (d) involves treating the industrial or environmental material with an agent that mitigates the presence of the acidic sulfide species.

Any suitable agent that mitigates the presence of the acid sulfide species may be used. The agent may react with the acidic sulfide species and/or it may otherwise interact with it in some way to make it less harmful. For example the agent may prevent the release of hydrogen sulfide gas by the acidic sulfide species. Suitable agents of this type will be known to the person skilled in the art.

The agent that mitigates the presence of the acidic sulfide species may be selected from: the condensation products of amines and formaldehyde; the condensation product of an amine and a carbonyl; aldehydes; ketones; metal salts; alkanolamines and their condensation products with a carbonyl or formaldeyde. Other reagents for treating acidic sulfide species will be known to the person skilled in the art. The skilled person would be able to select a suitable additive or combination of additives as appropriate, according to the application.

In some preferred embodiments the amount of agent used in step (d) may be determined with reference to the calculation carried out in step (c). In some embodiments steps (x), (a), (b) and (c) may be repeated following step (d) and step (d) only repeated if necessary.

The invention will now be further described with reference to the following non-limiting examples.

The method of the present invention was carried out as follows:

Spectroscopy Equipment

Any spectrophotometer capable of determining a change in absorbance or transmission at one or more wavelengths in the desired range may be used.

Synthesis of $H_2S$ Sensitive Dye

Copper(II) 1-(2-pyridylazo)-2-naphthol Dye 1-(2-pyridylazo)-2-naphthol (5.00 g, 20.1 mmol) was dissolved in EtOH (200 ml). A solution of $CuCl_2 \cdot 2H_2O$ (3.42 g, 20.1 mmol) in water (6 ml) was added and the resulting mixture stirred at room temperature for 2 hours. A dark red precipitate formed during the reaction which was collected by filtration, washed with ethanol and dried under vacuum to give Copper(II) 1-(2-pyridylazo)-2-naphthol as a dark red solid.

0.1M pH 7.2 Buffer

Tris(hydroxymethyl)aminomethane·HCl (15.38 g, 0.10 mol) was dissolved in 1 L of deionised water.

Copper(II) 1-(2-pyridylazo)-2-naphthol Dye Solution

Copper(II) 1-(2-pyridylazo)-2-naphthol dye (20.0 mg) was placed in a 1 L volumetric flask and ethanol (500 ml) was added. 100 ml of the buffer solution was added to a 1 L volumetric flask. The dye/buffer solution was made up to 1000 ml using ethanol, and the flask was shaken well to ensure that the dye had completely dissolved.

Preparation of $Na_2S$ Stock Solutions

A concentrated solution of 1 mg/ml $Na_2S \cdot xH_2O$ (60-63%, extra pure, scales, ACROS Organics™) in deionised water was prepared. Further dilute samples of the $Na_2S$ stock solution were prepared according to the ratios in table 1.

TABLE 1

| Ingredient ratios for stock solutions of sodium sulfide | | |
|---|---|---|
| Equivalent Concentration of $H_2S$ (mg/kg) | Concentrated $Na_2S$ stock solution (ml) | Deionised water (ml) |
| 0 | 0.00 ml | 3.00 ml |
| 8.7 | 0.10 ml | 2.90 ml |
| 17.5 | 0.20 ml | 2.80 ml |
| 26.2 | 0.30 ml | 2.70 ml |
| 34.9 | 0.40 ml | 2.60 ml |
| 43.7 | 0.50 ml | 2.50 ml |
| 52.4 | 0.60 ml | 2.40 ml |
| 61.1 | 0.70 ml | 2.30 ml |
| 68.9 | 0.80 ml | 2.20 ml |
| 78.6 | 0.90 ml | 2.10 ml |
| 87.3 | 1.00 ml | 2.00 ml |
| 109.2 | 1.25 ml | 1.75 ml |
| 131.0 | 1.50 ml | 1.50 ml |
| 174.7 | 2.00 ml | 1.00 ml |

Dye Calibration

Figure 1:
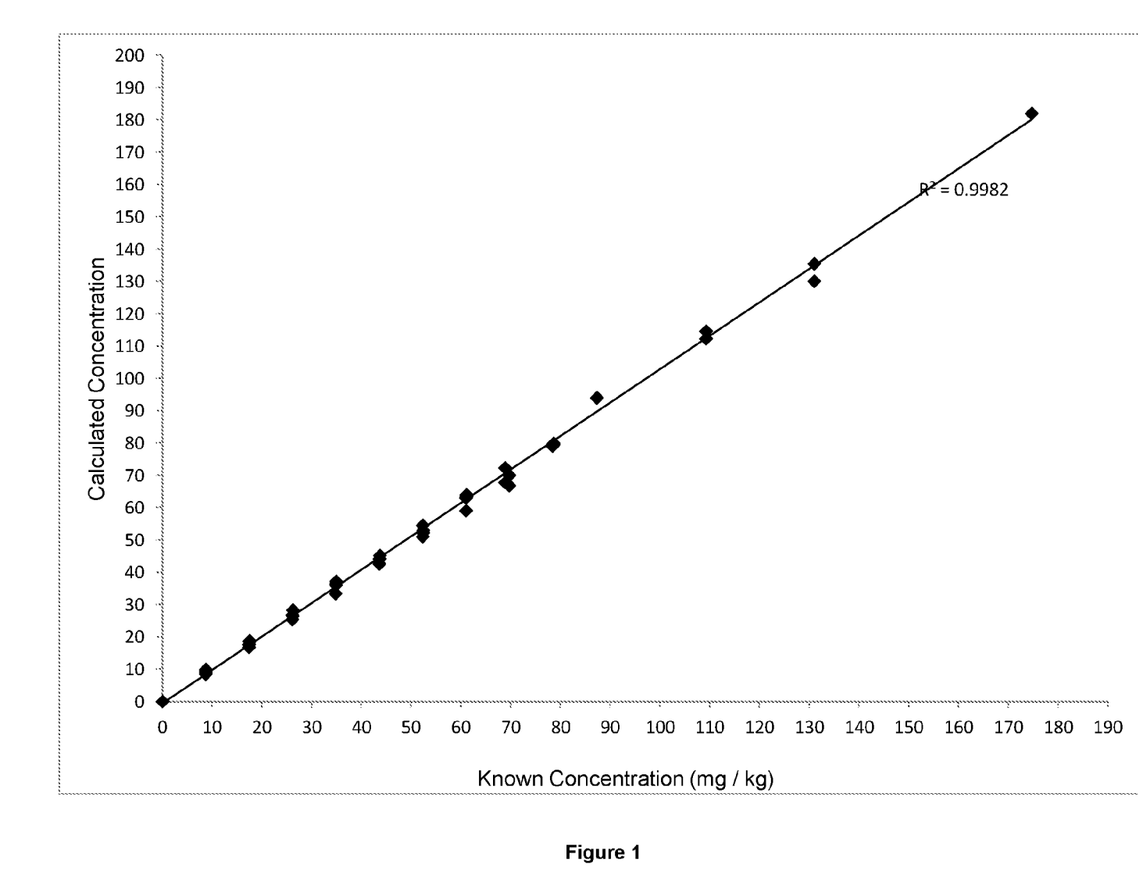
FIG. 1 depicts the linear correlation between absorbance and sulfide concentration.

A spectroscopy vial was pre-filled with copper(II) 1-(2-pyridylazo)-2-naphthol dye solution (10 ml) and the spectrometer's baseline set against the filled vial. Using a calibrated 20-200 µl pipette 100 µl of the first $Na_2S$ stock solution was transferred into the dye solution and the screw-top lid was closed. The vial was shaken vigorously for 3 seconds. The absorbance of the dye solution at 450 nm was read using the spectrometer. The reading was repeated with a fresh solution of dye for each concentration of $Na_2S$. The outcome was plotted (FIG. 1) to determine the linear correlation between absorbance and sulfide concentration.

Testing the $H_2S$ Content of Liquids

Qualitative Analysis of $H_2S$ in Colourless Solvents

A vial was pre-filled with copper(II) 1-(2-pyridylazo)-2-naphthol dye solution (4 ml). Using a syringe or pipette 0.3 ml of the liquid to be tested was extracted and transferred to the dye solution. The dye solution was shaken vigorously for 3 seconds and then the colour change observed.

Dye remains pink/red=little or no $H_2S$, sulfides or mercaptans are present (<1 mg/kg)

Dye turns orange/yellow=$H_2S$, sulfides or mercaptans are present (≥1 mg/kg)

Figure 2:
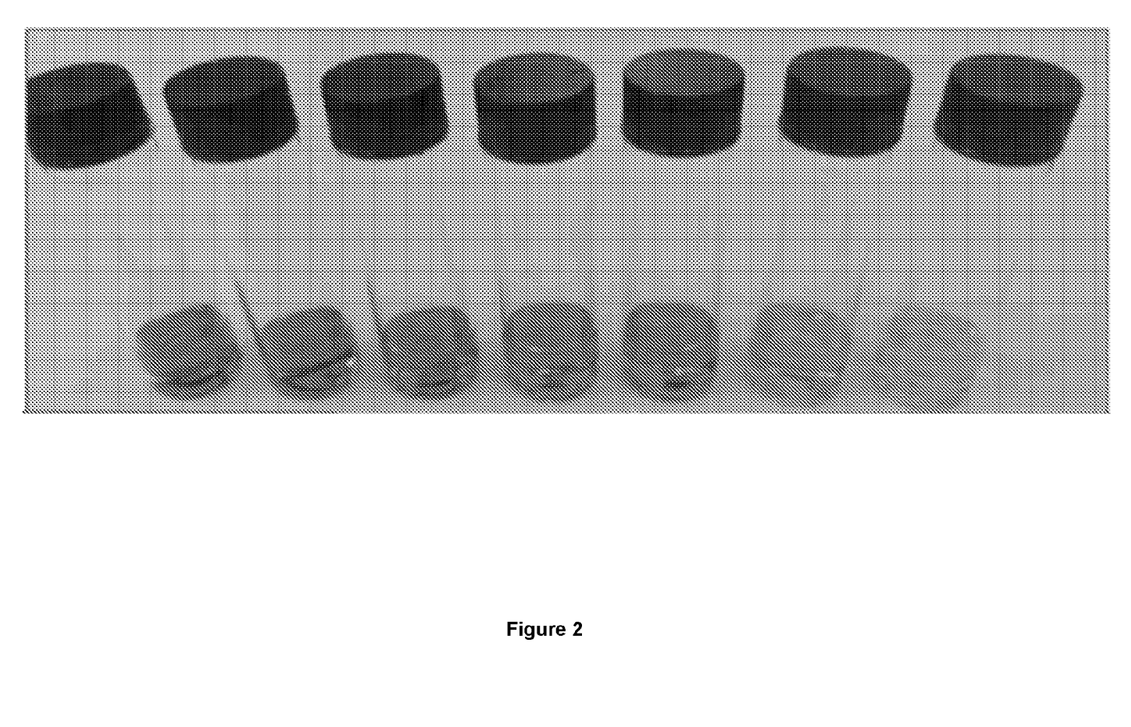
FIG. 2 shows the change in colour of the dye solution as it is reacted with sulfides.

FIG. 2 Shows the change in colour of the dye solution as it is reacted with sulfides.

Quantitative Analysis of $H_2S$ in Colourless Liquids

Figure 3:
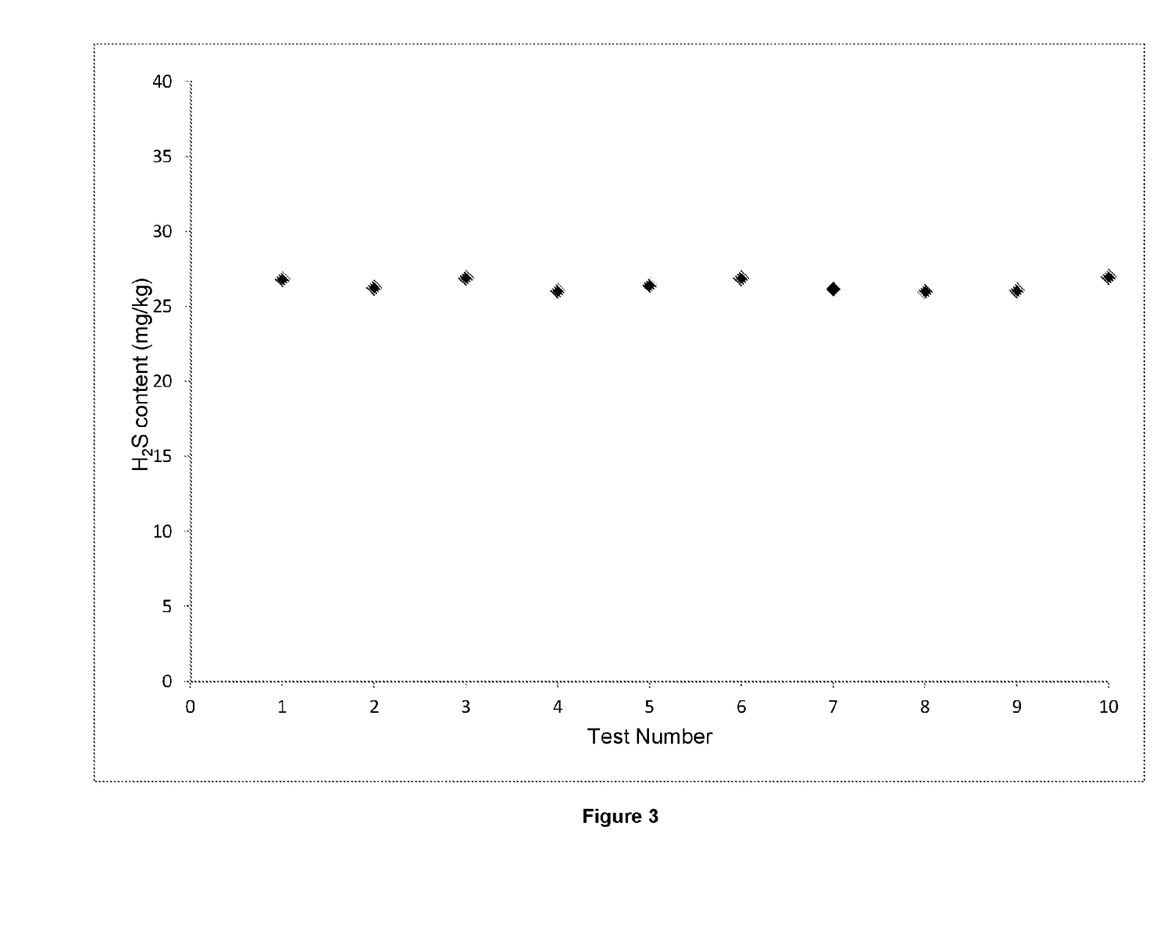
FIG. 3 shows quantitative analysis of $H_2S$ in colourless liquids.

A spectroscopy vial was pre-filled with copper(II) 1-(2-pyridylazo)-2-naphthol dye solution (10 ml) and the baseline of the spectrometer set against the filled vial. Using a syringe 0.1 ml of the liquid to be tested was extracted and transferred to the dye solution. The dye solution was shaken vigorously for 3 seconds then the absorbance of the dye solution at 450 nm read using the spectrometer. The $H_2S$ content of the liquid can now be calculated relative to a previously collected calibration curve, by inputting the reading into the smartphone application. The correlation of the results is shown in FIG. 3.

Quantitative Analysis of $H_2S$ in Coloured Liquids (e.g. Crude Oil)

Figure 4:
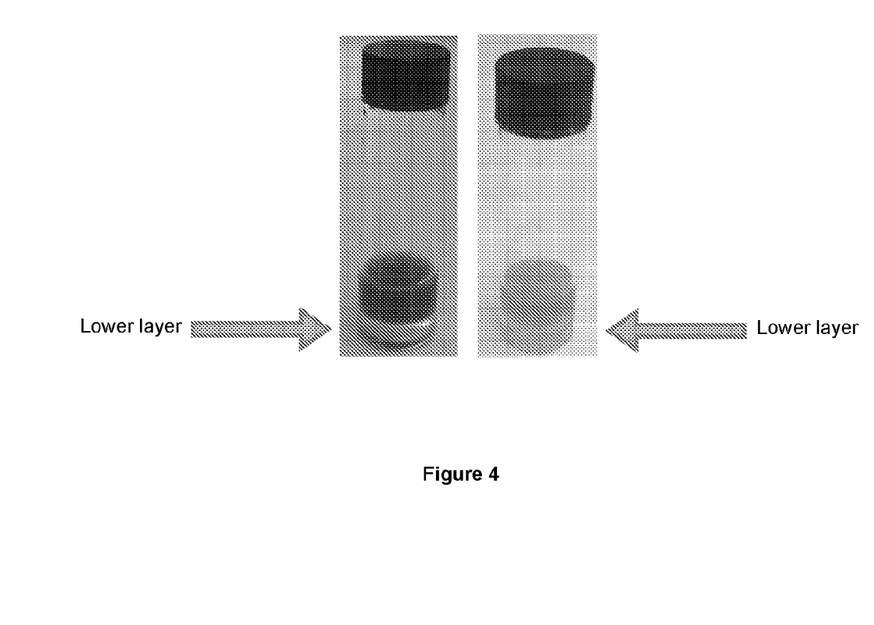
FIG. 4 is a photographic depiction of $H_2S$ in coloured liquids (e.g. crude oil)

A spectroscopy vial was pre-filled with copper(II) 1-(2-pyridylazo)-2-naphthol dye solution (10 ml) and the baseline of the spectrometer set against the filled vial. A 14 ml extraction vial was filled with NaOH solution (0.01M, 2 ml) and Caromax 20 (2 ml). The vial, cap and contents were weighed and then crude oil (ca. 2 ml) was added and the vial and contents re-weighed. The mass of crude oil used was recorded. The vial was shaken vigorously for 10 seconds then left to separate. Once two distinct layers had formed (1-10 minutes) the sample was ready to test (FIG. 4). Using a calibrated 20-200 µl pipette 100 µl of clear liquid was collected from the lower phase and transferred to the dye solution. The dye solution was shaken vigorously for 3 seconds then the absorbance of the dye solution at 450 nm read using the spectrometer. The value was inputted into the smartphone application to calculate the $H_2S$ content of the sample.

Figure 5:
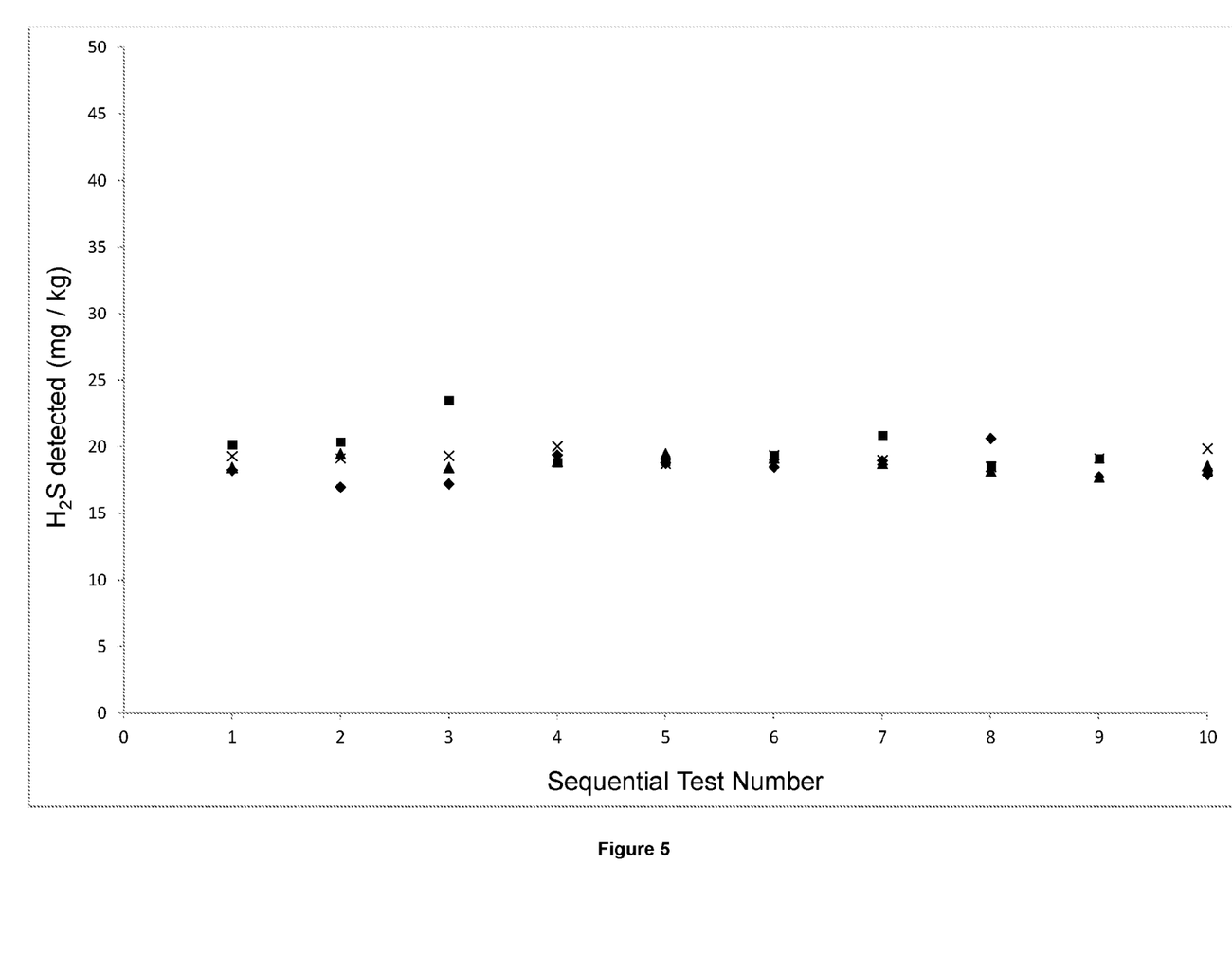
FIG. 5 is a graph depicting reliability of the method(s) for determining the presence of an acidic sulfide species in a liquid sample.

The reliability of the method was tested by asking multiple users to carry out 10 measurements. The results are shown in FIG. 5.

The invention claimed is:

1. A method for determining presence of an acidic sulfide species in a non-aqueous liquid sample of an industrial or environmental material, the method comprising the steps of:
   (a1) contacting the non-aqueous liquid sample with an extraction composition to form an aqueous phase and a non-aqueous phase, separating the aqueous and non-aqueous phases and collecting the aqueous phase or a portion thereof to provide an aqueous extract;
   (a2) contacting the aqueous extract with a liquid composition comprising a metal complex dye compound thereby forming a mixture; and
   (b) examining an electromagnetic absorption spectrum of the mixture obtained in step (a2) thereby quantitatively assessing whether any acidic sulfide species are present in the non-aqueous liquid sample,
   wherein the electromagnetic absorption spectrum of the metal complex dye compound changes upon reaction with an acidic sulfide species;
   wherein the industrial or environmental material are:
   fluids in or extracted from an oil well;
   products, by-products, intermediates, and waste streams from refineries and other industries;
   and
   wherein the metal complex dye compound is a copper complex of an azo dye; and
   wherein the extraction composition includes a basic aqueous component having a pH of at least 10.

2. The method according to claim 1, wherein the non-aqueous sample of an industrial or environmental material is crude oil and/or petroleum refinery liquids.

3. The method according to claim 1, wherein the extraction composition includes a non-aqueous component.

4. The method according to claim 1, wherein step (b) involves observing a color of the mixture.

5. The method according to claim 1, wherein step (b) involves comparing a color of the mixture obtained in step (a2) with a reference chart of results obtained using standard compositions.

6. The method according to claim 1, wherein step (b) involves measuring an intensity of light absorbed at a particular wavelength or wavelengths in the mixture obtained in step (a2).

7. The method according to claim 6, wherein the light intensity reading is entered into a device which is programmed to calculate the sulfide concentration and display the result.

8. A method of treating an industrial or environmental material to combat the presence of acidic sulfide species, the method comprising:
   (x) preparing a non-aqueous liquid sample of the industrial or environmental material;
   (a1) contacting the non-aqueous liquid sample with an extraction composition to form an aqueous phase and a non-aqueous phase, separating the aqueous and non-aqueous phases and collecting the aqueous phase or a portion thereof to provide an aqueous extract;
   (a2) contacting the aqueous extract with a liquid composition comprising a metal complex dye compound thereby forming a mixture; and
   (b) examining a changed region of the electromagnetic absorption spectrum of the mixture obtained in step (a2);
   (c) using the electromagnetic absorption spectrum examined in step (b) to calculate an amount of acidic sulfide species present in the non-aqueous liquid sample and in the industrial or environmental material; and
   (d) treating the industrial or environmental material with an agent that mitigates the presence of the acidic sulfide species,
   wherein the industrial or environmental material are:
   fluids in or extracted from an oil well;
   products, by-products, intermediates, and waste streams from refineries and other industries;
   and
   wherein the metal complex dye compound is a copper complex of an azo dye; and
   wherein the extraction composition includes a basic aqueous component having a pH of at least 10.

9. The method of treating an industrial or environmental material according to claim 8, wherein the industrial or environmental material is in and/or obtained from at least one of an oil well, a geothermal well, an oil rig, the cargo hold of a transport vehicle, a storage tank, or a point on a pipeline.

10. The method of claim 1, wherein the pH of the basic aqueous component ranges from 10 to 12.

11. The method of claim 10, wherein the method consists of steps (a1)-(b).

12. The method of claim 1, wherein the method consists of steps (a1)-(b).

13. The method of claim 8, wherein the pH of the basic aqueous component ranges from 10 to 12.

14. The method of claim 13, wherein the method consists of steps (a1)-(d).

15. The method of claim 8, wherein the method consists of steps (a1)-(d).

* * * * *